United States Patent [19]

Zoubek et al.

[11] Patent Number: 5,114,722
[45] Date of Patent: May 19, 1992

[54] MEDICAMENT FROM PEYER'S PATCHES

[76] Inventors: Eugen Zoubek, Allescherstrasse 2a, 8000 Munchen 71; Heinrich Kehlbeck, Bahnhofstrasse, 2812 Hoya, both of Fed. Rep. of Germany

[21] Appl. No.: 607,595

[22] Filed: Oct. 31, 1990

Related U.S. Application Data

[63] Continuation of Ser. No. 351,966, May 15, 1989, abandoned.

[30] Foreign Application Priority Data

May 20, 1988 [DE] Fed. Rep. of Germany ....... 3817360

[51] Int. Cl.⁵ .............................................. A61K 35/38
[52] U.S. Cl. ................................... 424/551; 424/520; 424/578
[58] Field of Search ........................ 424/520, 551, 578

[56] References Cited

U.S. PATENT DOCUMENTS 4,377,514  3/1983  Ruhenstroth-Bauer ............ 424/578

FOREIGN PATENT DOCUMENTS 3443411  5/1986  Fed. Rep. of Germany .

*Primary Examiner*—Douglas W. Robinson
*Assistant Examiner*—Jean C. Witz
*Attorney, Agent, or Firm*—Learman & McCulloch

[57] ABSTRACT

The invention relates to a medicament in the form of a lyophilisate produced from a total extract from Peyer's patches, preferably in homoeopathic dilution. It can be used advantageously for the improvement of the humoral defence system.

5 Claims, No Drawings

MEDICAMENT FROM PEYER'S PATCHES

This is a continuation of copending application Ser. No. 07/351,966 filed on May 15, 1989 now abandoned.

The invention relates to a novel medicament, advantageous applications of this medicament and a method for the production thereof.

The subject matter of German Patent Application No. P 34 43 411.9 and of European Patent Application No. 0 183 253 is a medicament in the form of an organ extract produced from Peyer's patches.

As is set out in detail in those patent applications, the Peyer's patches are closely linked to the immune system and play a decisive part in the make-up of the immune system. Numerous findings emphasize that the Peyer's patches do not only have a peripheral importance. This relatively large mass of lymph nodes also fulfils a central and immunoregulatory role for the entire organism.

It is known from European Patent No. 0 049 379 that a factor of hormonal structure, namely a factor which stimulates the rate of proliferation of liver cells, can be isolated from the Peyer's patches.

The object of the subject invention is to:
- make further developments to the medicament according to German Patent Application No. P 34 43 411.9 and European Patent Application No. 0 183 253 so that it has an improved effectiveness while at the same time showing good tolerance,
- provide advantageous applications of this medicament,
- and to develop a suitable method for the production thereof.

In the further development of the medicament proposed in German Patent Application No. P 34 43 411.9 and in European Patent Application No. 0 183 253 it has proved important to produce from Peyer's patches a lyophilisate which is either used as an allopathic preparation (or as a constituent of such a preparation) or is used particularly advantageously as primary substance for the production of homoeopathic preparations.

According to the invention the lyophilisate either contains the total extract of Peyer's patches or only certain thermolabile proteins are precipitated out of this total extract by a heating step and filtered off.

The medicament according to the invention is advantageously produced as follows:

For the production of the total extract from the Peyer's patches organically sound calves are used which have undergone health checks during rearing and slaughter. Immediately after slaughter the Peyer's patches such as the small intestines are removed by experienced veterinary surgeons, cleaned carefully and frozen rapidly in liquid nitrogen. Later the Peyer's patches are thawed and rinsed in sterile 0.9% sodium chloride solution until they are absolutely clean. Any connective or adipose tissue adhering to them is removed. The organ parts are homogenised in a mixer for 30 seconds. Of the resulting homogenisate one part is suspended in 2.5 parts of clean water (DAB 9), which has been cooled to 4°-8° C., and extracted while stirring at 4°-8° for 60 minutes.

Thereafter the solution is decanted through surgical muslin made from cotton (DAB 9) and centrifuged by means of a continuous centrifuge at 17,000 g with a through flow rate of 5 l/h. (DAB is defined in the German Book of Homoeopathic Medicine). The resulting substance is pre-filtered through a membrane filter made from glass fiber material and subjected to sterile filtration with a polyvinylidene fluoride membrane filter (0.2 μm pore size). In a variant the water is removed from the sterile-filtered organ extract by lyophilisation. The latter takes place after freezing of the extract at −50° C. in a vacuum of at most 0.4 mbar (corresponding to an ice temperature of −30° C.) with simultaneous heating of the drying chamber to 28°-32° C.).

In the preferred variant the sterile-filtered solution is boiled at 100° C. for 30 minutes. The precipitated proteins are filtered off, whereupon the lyophilisation takes place under the conditions described above.

Convincing results as regards stability, effectiveness etc. were obtained in extensive series of tests in the application of the lyophilisate in the form of capsules, ointments, suppositories, injections, drops and tablets.

A pharmacological and toxicological examination of the lyophilisate of a total extract from the Peyer's patches showed that after one single intramuscular application on a rat the test substance did not produce any clinical toxicological symptoms.

A medicament in the form of a lyophilisate produced from the Peyer's patches can be used in allopathic form or preferably in homoeopathic form particularly for the following therapeutic purposes:
- for the treatment of inflammations, especially chronic and recurrent inflammations in which there are defects of the humoral defence,
- for the immunomodulation of the humoral immunity,
- for the treatment of gastro-intestinal illnesses, such as ulcus ventriculi, ulcus duodeni, colitis ulcerosa, morbus Crohn, diverticulitis and pancreatitis,
- for the treatment of psoriasis,
- for the supportive treatment of diabetes mellitus,
- for the treatment of atrophy of the gastric mucosa, particularly stomach resections due to carcinoma of the stomach or gastric ulcers,
- for the treatment of allergies.

It has also proved advantageous to use the medicament according to the invention in conjunction with thymus organ extract.

Where "Rebas" is named as a constituent in the medicament compositions and substances referred to hereinafter, this is a lyophilisate of the total extract from Peyer's patches in homoeopathic dilution (for example in the homoeopathic potency D4), having the thermolabile portions removed or set forth herein; D1, D2 etc. characterizing the homeopathic dilution in accordance with the German Bouh of Homeopathic Medicine, corresponding to 1x, 2x, etc, respectively, in the United States.

The following examples are given in order to illustrate the therapeutic results which were obtained with an allopathic form of the lyophilisate produced from the total extract from the Peyer's patches:

1. In a case of severe atrophy of the stomach which occurred two years after a stomach resection due to carcinoma of the stomach, the patient was treated exclusively with an extract according to the invention in doses of 5×1 ml to 5×4 ml daily for four weeks. Even after the first week there was a fundamental improvement. As the treatment progressed all the subjective and objective pathological phenomena were able to be eliminated.

2. In a case of morbus Crohn which had existed for five years, activity index according to Best 153, weight 62 kg, BKS 24/56 at the beginning of the treatment, after treatment for 18 months with the extract according to the invention the result was an activity index according to Best 11, weight 72 kg, Blutkörperchensenkungsreaktion (translated as erythrocytes sinking reaction used for measuring the sinking velocity of erythrocytes in a small glass tube within a unit time of one to two hours for diagnostic blood teating) (BKS) §; after several months no more treatment was necessary.

3. A 48-year-old patient suffered for three years from diabetes mellitus: blood sugar 280 mg %, and disturbed sleep. After two injection treatments each at four weeks with the extract according to the invention (and changing to a high-roughage diet), within four and a half months the blood sugar fell to 130 mg %, with no more disturbance of sleep.

The therapeutic results obtained with the homeopathic form of the lyophilised total extract from the Peyer's patches (Rebas) are particularly surprising. They will be explained with the aid of the following examples:

1. A 74-year-old patient had suffered for a year and a half, above all at night, from chronic laryngitis with irritation of the throat and a tickling feeling in the larynx. In the mornings he brought up purulent phlegm, and at times he was hoarse. There were inflamed scars after an abscess tonsillectomy (45 years ago). After eight injections with Rebas D12, mixed with the lymph agent *injectio lymphatica*, into the tonsillectomy scars all the pathological phenomena disappeared. The lymph agent alone had not previously shown any effect.

2. Rheumatoid arthritis in the right hand joint and the right elbow joint as well as considerable coxitis on the left had existed for five years in a 40-year-old patient; BKS 24/55. In-patient treatment in a Munich university clinic did not achieve success. The pains increased in the left hip joint until they became unbearable so that during and after the in-patient treatment the patient could only move about with the aid of crutches. A marked restriction of movement with rotation destroyed was confirmed by an orthopaedic investigation. From the orthopaedic side an operative therapy for the coxitis with TEP was proposed in the long term. There was also an allergy. Biological treatment produced only limited success. Only the treatment with the extract according to the invention produced significant success.

The patient can again walk without crutches and go for long walks. There is no restriction of movement in the left hip joint and the pain is gone.

3. In a 65-year-old patient there was an acute incidence of allergy with extensive swelling and reddening over the entire body. He had never suffered from allergic phenomena previously. With Rebas D12 and later Rebas D4 subcutaneously into the acupuncture points all the allergic phenoma disappeared immediately.

4. In a 12-year-old girl the humoral immune defence was severely lowered. Cold followed cold—often with highly feverish phases, so that the family doctor frequently used antibiotics. The tonsils were greatly enlarged and had suppurations on the left. In the blood picture a leucocytosis was established with a reduced monocyte count. The subacute inflammations were treated orally in addition to 1 g Vitamin C twice daily. She changed to a biological whole-grain diet. 2 weeks later a course of Rebas was commenced, one capsule D4 being administered twice daily and one REBAS D3 suppository daily. After only a few weeks all the inflammation symptoms had subsided and the blood picture had normalised. No further infections occurred.

What is claimed is:

1. A medicament composition made by the process of: homogenizing Peyer's patches, preparing water extract from the homogenized Peyer's patches, the method characterized by heating the extract for about 30 minutes at 100° C. and forming a lyophilisate for preparation in homeopathic form.

2. The composition of claim 1 which is in allopathic form.

3. The composition of claim 1 combined with thymus organ extract.

4. A method of preparing a medicament composition comprising preparing a water extract of homogenized Peyer's patches, subjecting said extract to sterile filtration, heating the sterile-filtered extract to 100° C. for 30 minutes to precipitate thermolabile proteins, and removing said proteins by filtration.

5. The method of claim 4 wherein said resulting extract is further subjected to lyophilisation.

* * * * *